United States Patent

Fahle et al.

[11] Patent Number: 5,920,375
[45] Date of Patent: Jul. 6, 1999

[54] PROCESS FOR MEASURING THE VISUAL FIELD RECOGNIZABLE BY THE EYE OF A PATIENT

[75] Inventors: Manfred Fahle, Tuebingen; Gert Koest, Hanover, both of Germany

[73] Assignee: Oculus Optikgeraete GmbH, Wetzlar, Germany

[21] Appl. No.: 08/909,606

[22] Filed: Aug. 12, 1997

[51] Int. Cl.$^6$ .................................................. A61B 3/00

[52] U.S. Cl. ............................................ 351/246; 351/224

[58] Field of Search ................................... 351/222, 224, 351/226, 246

[56] References Cited

U.S. PATENT DOCUMENTS 5,565,949   10/1996   Kasha, Jr. ............................ 351/224

*Primary Examiner*—Huy Mai
*Attorney, Agent, or Firm*—Flynn, Thiel, Boutell & Tanis, P.C.

[57] ABSTRACT

A perimetric structure and a testing process having a digitalized camera mechanism for storing the image and evaluating with a visual field testing device, in which the individual testing points of varying size and varying contrast are sequentially offered to the patient for viewing. The testing points can be projected in a sphere or on a screen or can be offered on a monitor. The visual field is tested by registration of eye movements (saccades), which the person being tested carries out at presented testing points, as soon as he/she can recognize them.

7 Claims, 3 Drawing Sheets

PROCESS FOR MEASURING THE VISUAL FIELD RECOGNIZABLE BY THE EYE OF A PATIENT

FIELD OF THE INVENTION

The invention relates to a process for measuring the visual field recognizable by the eye of a patient by means for a fixation point for the eye, which fixation point is projected onto an image plane, is presented to the patient and the eye of the patient is aimed by the patient at the fixation point, and a perimeter for carrying out such a process.

BACKGROUND OF THE INVENTION

Such a visual field determination is carried out by means of a perimeter in such a manner that the patient rigidly fixes a fixed point, a so-called fixation point, faded in on an image plane; at the same time testing points are offered to the patient at various areas of the visual field, and the patient is then supposed to indicate by pressing a key or verbally whether he/she recognizes the respective testing point. The offering of the testing points is done either manually or automatically, the result of the measurement is subsequently entered into a test protocol or is manually or automatically registered, processed and printed out by a computer.

This testing process is stressful in particular for older patients since the examination of many visual field positions requires a longer period of time and the rigid fixation of a fixation point is nonphysiological, tiresome and uncomfortable.

SUMMARY OF THE INVENTION

The invention therefore has the purpose to overcome these deficiencies and to develop a process of the type identified in detail above including an associated perimeter in such a manner that it presents little stress for the patient and results quickly in mechanically evaluatable results.

According to the invention the purpose is attained first by a process, in which after aiming of the eye by the patient at the fixation point a new fixation point is thereafter projected to a position on the image plane, which is different from the original fixation point, is aimed by the patient by means of a saccade, and this saccade is thereafter measured, whereby the new fixation point forms now the original fixation point for a new saccade to a further fixation point, and these process steps are sequentially repeated as needed by projecting further fixation points to the image plane.

The otherwise presented testing points, which serve the pure visual field testing and are not aimed by the patient, are here replaced with sequentially offered, in each case newly aimed fixation points so that difficult viewing of a testing point with a simultaneous aiming for a fixation point can be deleted.

The patient is asked to look to the respective new fixation point, which means to carry out a sudden eye movement, a so-called saccade, toward the new fixation point. The succession of the fixation points and the associated saccades or rather missing reactions of the patient (when a new fixation point lies outside of his field of vision) are stored in a computer and deliver the basis for the calculation and illustration of the visual field or of a visual field defect after the process has been concluded. The result of measurement can then be called up per monitor or printer.

Initially not recognized fixation points, which therefore were not aimed for by a saccade, are later again tested at the same point of the image plane with an increased intensity, greater contrast, over a longer period of time, etc. in order to carry out a threshold determination.

A testing process carried out in this manner shortens the testing time in comparison to the use of testing points to approximately half of its time because the saccades can quickly follow one after the other.

It is particularly advantageous when the original fixation point is cancelled simultaneously with or after the projecting of the new fixation point; as a control, however, it is also possible to offer the original fixation point as long as or until the new fixation point has safely been aimed for by the patient.

The coordinate system of the patient and of the computer is each shifted by the saccades, which is compensated for by a computer program.

Furthermore the invention is characterized by a perimeter for carrying out the process, in which an image plane, for example a videomonitor or a perimetric hemisphere, is provided for producing the fixation points.

The offering of the fixation points occurs thereby either on the videomonitor (in grey steps or in color) or by means of projection through a suitable projection system, which can illuminate, for example, through moved mirrors and/or prisms and/or through individually controllable photoconductors, various positions on a testing screen or in a perimetric hemisphere. By attaching shutters of light sources the length of the offering can be varied; the luminous density can be influenced by grey filters, or through color filters, the composition (namely the color) of the light for the fixation points.

Important is the registration of the position of the eye of the patient, for which several possibilities can be utilized. It can occur principally with the help of the derivation of the dipole of the eye (EOG), even though this method demands repeated readjustments and requires the mounting of electrodes next to the eyes. A further method is to apply a contact lens with a built-in coil or built-in mirror, which permits a very exact determining of the eye position by applying a magnetic field to the coil or by illuminating the mirror with a laser, however, this method appears little suited for routine examinations.

A much better method is the reproduction of the eye on a CCD-Chip (charge coupled device) with a camera mechanism with at least one videocamera and the determination of the eye position by feeding the video images into a computer on a digital basis. Various strategies can thereby be pursued: Either simply determine of the edge of the corneal or of the pupil (a disadvantage being the nondifferentiatability of the head and eye movements) or the registration of this edge relative to the mirror image of an (infrared) illuminating source on the corneal (first Purkinje small mirror image).

BRIEF DESCRIPTION OF THE DRAWINGS

The invention will be discussed in greater detail hereinafter in connection with the drawings, in which.

DETAILED DESCRIPTION

Figure 1:
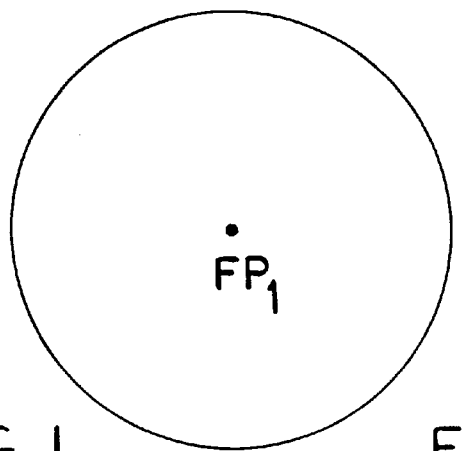
FIGS. 1 to 4 show image planes of a perimeter according to the invention, which image planes are offered to the patient.
Figure 2:
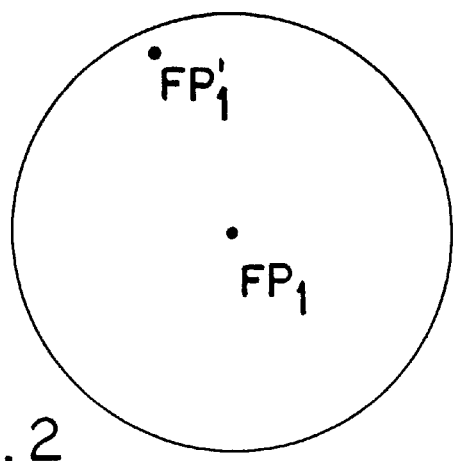
Figure 3:
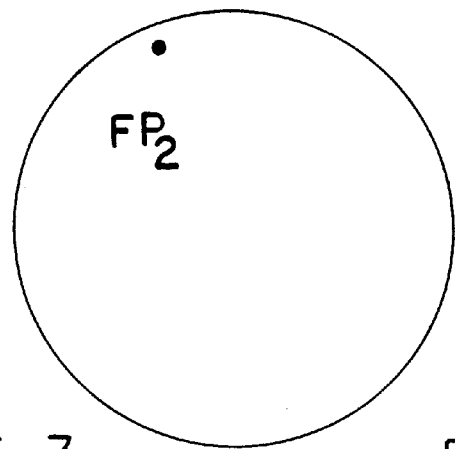
Figure 4:
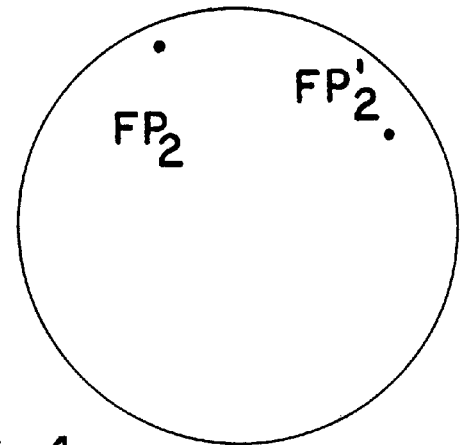
Figure 5:
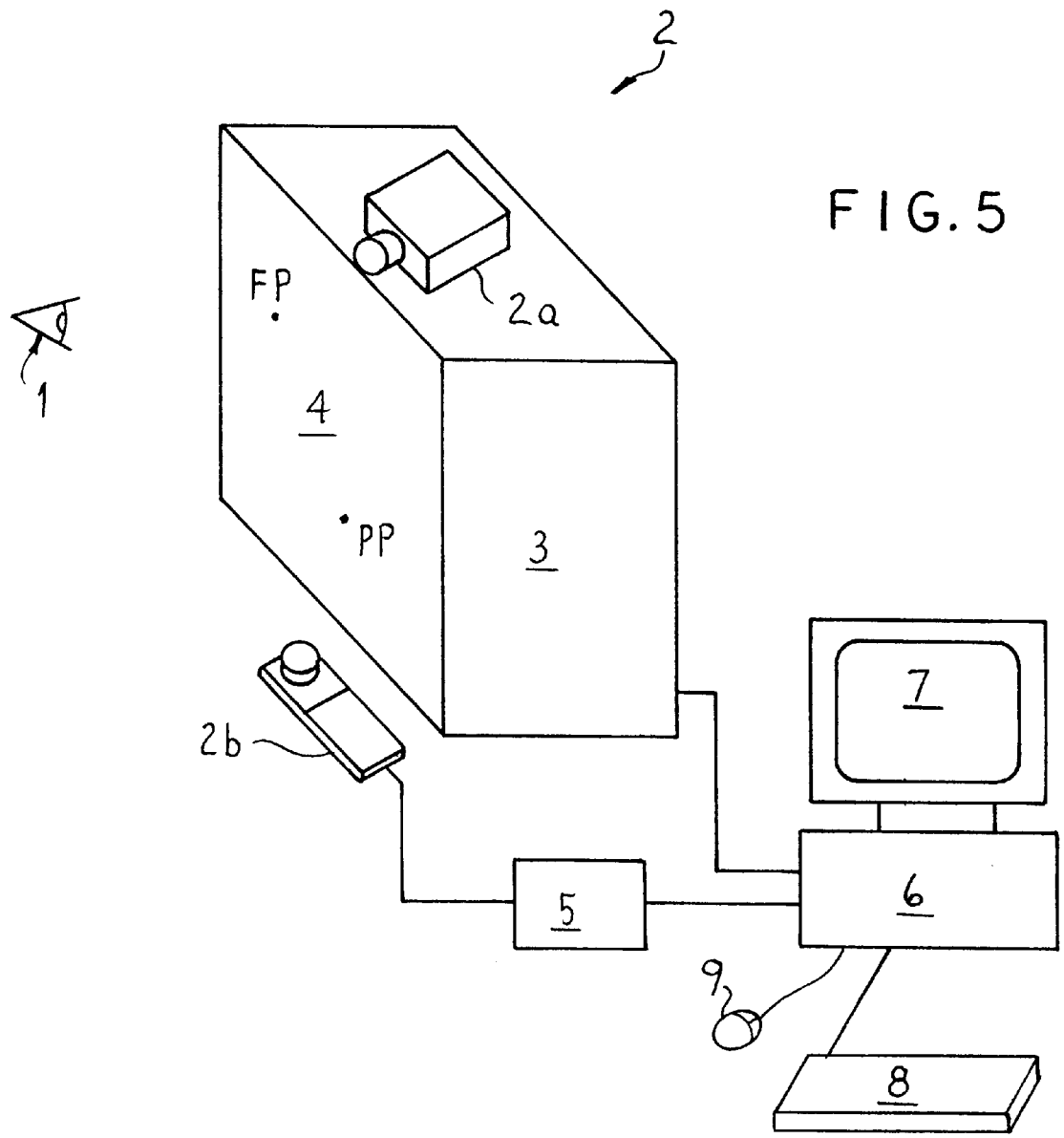
FIG. 5 shows a perimeter according to the invention with a videomonitor.

FIGS. 1–4 each illustrate one image plane 4 at successive points of time. FIG. 1 shows a first fixation point $FP_1$ at a first point of time, which fixation point is fixed by the patient 1 (FIG. 5). A second fixation point $FP_1'$ is fed into the timewise directly following image plane 4 of FIG. 2, which fixation point can initially serve as the testing point for the patient, as this is common in the state of the art. However, the patient 1 aims thereafter, after one saccade, directly for the second fixation point $FP_1'$, whereby the saccade is measured and registered by an apparatus. The original fixation point $FP_1$ disappears at the following point of time in FIG. 3, and the second fixation point $FP_1'$, which continues to exist, forms now a new (original) fixation point $FP_2$, from where (FIG. 4) a new saccade leads to a further (new) fixation point $FP_2'$, which is again measured and registered by an apparatus. The fixation point $FP_2'$ mutates without any further change thereafter (no longer illustrated in the drawing) to a further (original) fixation point $FP_3$, etc. The process continues so long or is repeated at certain points on the image plane 4 until the visual field of the patient is determined to a desired scope and with sufficient exactness.

Figure 6:
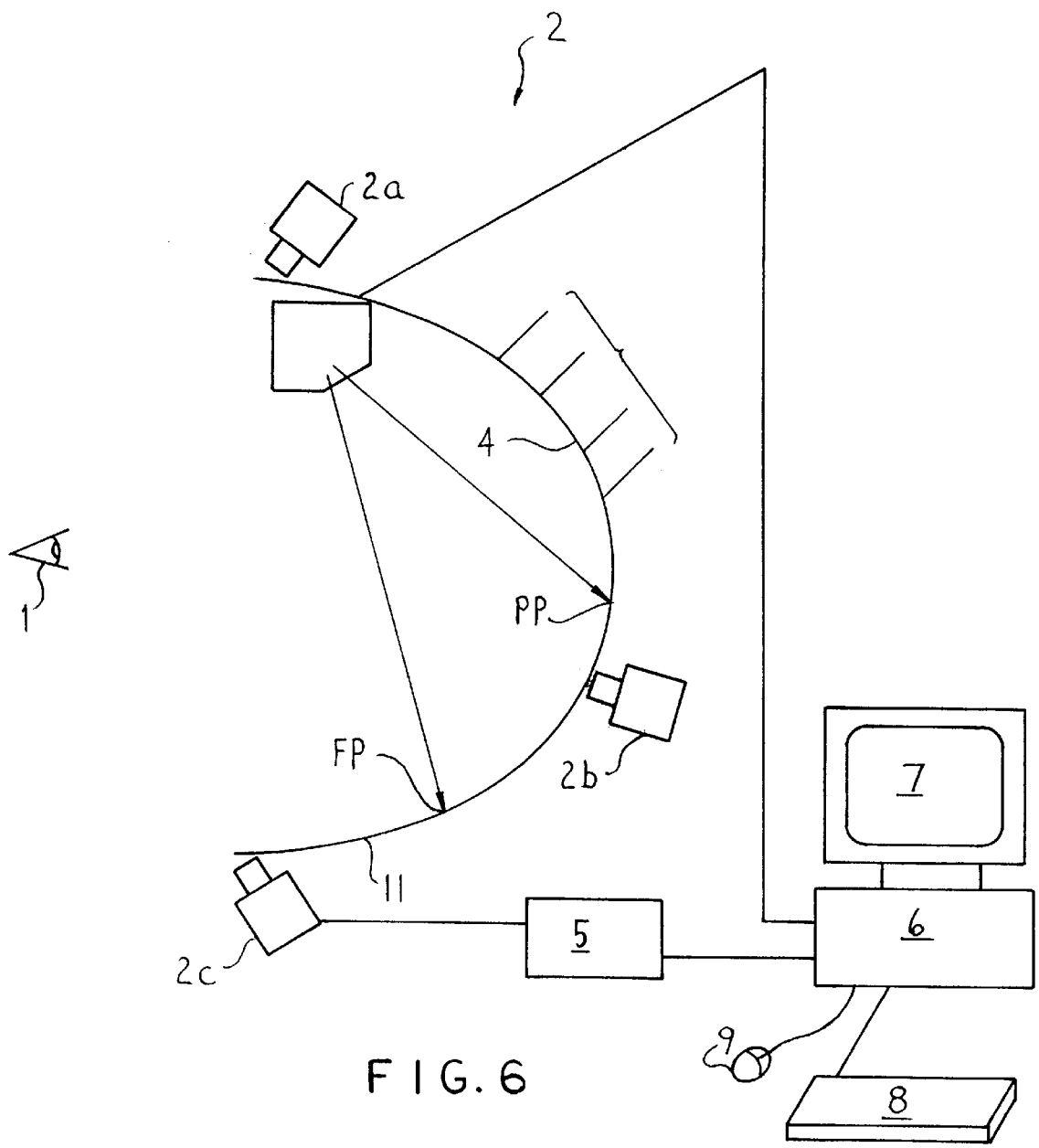
FIG. 6 shows a perimeter according to the invention with a perimetric hemisphere for creating an image plane, all in a simplified schematic illustration.

Devices suited for the process of the invention are disclosed in FIGS. 5 and 6.

The eye of the patient 1 is placed in FIG. 5 in front of a videomonitor 4 so that the videocameras 2a or 2b of a camera mechanism 2 can photograph the eye. The so taken picture of the eye is digitalized in a digitalizing device 5 and is fed to the computer 6.

The computer 6 analyzes the eye position and generates, program-controlled, the fixation points FP on the videomonitor 3.

The results of measurement can be displayed on the monitor 7 of the computer 6. A keyboard 8 or a mouse 9 permit the interactive operation.

The eye of the patient 1 is in FIG. 6 placed in front of a perimetric hemisphere 11 in such a manner that videocameras 2a, 2b and 2c of a camera mechanism 2 can take a picture of the eye. The results of the measurement are processed like in the case of the videomonitor 3 of FIG. 5 by the digitalizing device 5, the computer 6, etc. The computer 6 generates also the sequence and position of the fixation points FP on the hemisphere 11. Projection systems, photoconductors, small lamps, luminous diodes, etc. can be used for this purpose. The evaluation is done in the same manner as during the use of the videomonitor 3 of FIG. 5.

The embodiments of the invention in which an exclusive property or privilege is claimed are defined as follows:

1. In a process for measuring the visual field recognizable by the eye of a patient by means of a fixation point ($FP_1$) for the eye, which fixation point is projected onto an image plane and is presented to the patient for viewing and wherein the eye is aimed by the patient at the fixation point, the improvement comprising the steps of thereafter projecting a new fixation point ($FP_1'$) to a position on the image plane different from the original fixation point ($FP_1$), the eye is thereafter aimed at this new fixation point by the patient by means of a saccade, and this saccade is thereafter measured, whereby the new fixation point ($FP_1'$) forms now the original fixation point ($FP_2$) for a new saccade to a further fixation point ($FP_2'$), and these process steps are sequentially repeated as needed by projecting further fixation points ($FP_i$, $FP_i'$; i=1,2,3,4. . . n; n random).

2. The process according to claim 1, wherein in the measuring step the original fixation point ($FP_1$) is cancelled at the same time or after the projecting of the new fixation point ($FP_1'$).

3. The process according to claim 2, wherein the saccades carried out by the eye of the patient are measured by means of a camera mechanism consisting of at least one videocamera.

4. The process according to claim 1, wherein the saccades carried out by the eye of the patient are measured by means of a camera mechanism consisting of at least one videocamera.

5. The process according to claim 4, wherein in the measuring step the measuring signals obtained from the camera mechanism are digitalized.

6. The process according to claim 5, wherein the measuring signals are stored in a computer, are prepared for a measurement result, are illustrated on a monitor, and are printed by a printer.

7. The process according to claim 4, wherein the measuring signals are stored in a computer, are prepared for a measurement result, are illustrated on a monitor, and are printed by a printer.

* * * * *